US008992984B1

(12) United States Patent
Brinker et al.

(10) Patent No.: US 8,992,984 B1
(45) Date of Patent: Mar. 31, 2015

(54) PROTOCELLS AND THEIR USE FOR TARGETED DELIVERY OF MULTICOMPONENT CARGOS TO CANCER CELLS

(75) Inventors: C. Jeffrey Brinker, Albuquerque, NM (US); Carlee Erin Ashley, Albuquerque, NM (US); Xingmao Jiang, Albuquerque, NM (US); Juewen Liu, Kitchener (CA); David S. Peabody, Albuquerque, NM (US); Walker Richard Wharton, Corrales, NM (US); Eric Carnes, Albuquerque, NM (US); Bryce Chackerian, Albuquerque, NM (US); Cheryl L. Willman, Albuquerque, NM (US)

(73) Assignees: STC.UNM, Albuquergue, NM (US); Sandia Corporation, Albuquerque, NM (US)

( * ) Notice: Subject to any disclaimer, the term of this patent is extended or adjusted under 35 U.S.C. 154(b) by 777 days.

(21) Appl. No.: 12/909,572

(22) Filed: Oct. 21, 2010

Related U.S. Application Data

(60) Provisional application No. 61/279,438, filed on Oct. 21, 2009, provisional application No. 61/306,123, filed on Feb. 19, 2010.

(51) Int. Cl.
  *A61K 9/14* (2006.01)
  *A61K 9/51* (2006.01)
(52) U.S. Cl.
  CPC .................................. *A61K 9/5123* (2013.01)
  USPC ............ 424/490; 424/489; 424/400; 424/491
(58) Field of Classification Search
  USPC ................................... 977/721, 705; 424/400
  See application file for complete search history.

(56) References Cited

U.S. PATENT DOCUMENTS

| 7,514,267 | B1 | 4/2009 | Lopez et al. | |
|---|---|---|---|---|
| 8,734,816 | B2 | 5/2014 | Liu et al. | |
| 2008/0095852 | A1 | 4/2008 | Kong et al. | |
| 2011/0059156 | A9* | 3/2011 | Mirkin et al. | 424/450 |
| 2011/0097819 | A1* | 4/2011 | Groves et al. | 436/503 |
| 2011/0135571 | A1* | 6/2011 | Lin et al. | 424/1.65 |
| 2011/0268791 | A1* | 11/2011 | Liu et al. | 424/450 |
| 2014/0079774 | A1 | 3/2014 | Brinker et al. | |

FOREIGN PATENT DOCUMENTS

| WO | 03055469 | A1 | 7/2003 |
|---|---|---|---|
| WO | 2005009602 | A2 | 2/2005 |
| WO | 2010/078569 | A2 | 7/2010 |
| WO | 2012149376 | | 11/2012 |
| WO | 2013012891 | A1 | 1/2013 |
| WO | 2013056132 | A2 | 4/2013 |

OTHER PUBLICATIONS

Liu (J Am. Chem. Soc. 131, 1354-1355, 2009).*
Jain, Rakesh K. Barriers to Drug Delivery in Solid Tumors. Scientific American, 1994; pp. 58-65.
Sapra, Puja; Allen, Theresa M. Internalizing Antibodies are Necessary for Improved Therapeutic Efficacy of Antibody-targeted Liposomal Drugs. Cancer Res, 2002;62:7190-7194.
Torchilin, Vladimir P. Recent Advances With Liposomes as Pharmaceutical Carriers. Nature Reviews, 2005;4:145-159.
Pastan, Ira; Hassan, Raffit; Fitzgerald, David J; Kreitman, Roberts J. Immunotoxin therapy of cancer. Nature Reviews, 2006;6:559-565.
Gordon, Alan N; et al. Recurrent Epithelial Ovarian Carcinoma: A Randomized PHase III Study of Pegylated Liposomal Doxorubicin Versus Topotecan. Journal of Clinical Oncology, 2001;19(14):3312-3322.
Midoux, Patrick, et al. Membrane Permeabilization and Efficient Gene Transfer by a Peptide Containing Several Histidines. Bioconjugate Chem, 1998;9:260-267.
Liu, Juewen; Jiang, Xingmao; Ashley, Carlee; Brinker, Jeffrey C. Electrostatically Mediated Liposome Fusion and Lipid Exchange with a Nanoparticle-Supported Bilayer for Control of Surface Charge, Drug Containment, and Delivery. J Am Chem Soc, 2009;131:7567-7569.
Ashley, Carlee E; et al. The targeted delivery of multicomponent cargos to cancer cells by nanoporous particle-supported lipid bilayers. Nature Materials, 2011;10:389-397.
Soderquist et al.; Microparticle-mediated delivery of interleukin-10 plasmid DNA for the treatment of neuropathic pain. Poster Abstract No. 206d, 1 page, May 2008.
Milligan E.D. et al.; Intrathecal polymer-based interleukin-10 gene delivery for neuropathic pain. Neuron Glia Biology 2007, 2:1-16.
Bennett GJ, et al.; A peripheral mononeuropathy in rat that produces disorders of pain sensation like those seen in man. Pain 1988, 33:87-107.
Chacur M, et al.; A new model of sciatic inflammatory neuritis (SIN): induction of unilateral and bilateral mechanical allodynia following acute unilateral peri-sciatic immune activation in rats. Pain 2001, 94:231-244.
Milligan ED, et al.; Thermal hyperalgesia and mechanical allodynia produced by intrathecal administration of the human immunodeficiency virus-1 (HIV-1) envelope glycoprotein, gp120. Brain Research 2000, 861:105-116.
Milligan ED, et al.; Pathological and protective roles of glia in chronic pain. Nature Reviews Neuroscience Jan. 2009, 10:23-36.
Sloane E, et al.; Chronic constriction injury induced pathological pain states are controlled long term via intrathecal administration of a non-viral vector (NVV) encoding the anti-inflammatory cytokine interleukin-10 (IL-10). IN: Second Joint Scientific Meeting of the American Pain Society and the Canadian Pain Society (Gebhart GF, ed), (2004) p. 15: Chruchill Livingstone.

(Continued)

*Primary Examiner* — David Lukton
(74) *Attorney, Agent, or Firm* — Henry D. Coleman; R. Neil Sudol

(57) ABSTRACT

Various embodiments provide materials and methods for synthesizing protocells for use in targeted delivery of cargo components to cancer cells. In one embodiment, the lipid bilayer can be fused to the porous particle core to form a protocell. The lipid bilayer can be modified with targeting ligands or other ligands to achieve targeted delivery of cargo components that are loaded within the protocell to a target cell, e.g., a type of cancer. Shielding materials can be conjugated to the surface of the lipid bilayer to reduce undesired non-specific binding.

17 Claims, 6 Drawing Sheets

(56) References Cited

OTHER PUBLICATIONS

Juewen Liu, et al.; Silica nanoparticle supported lipid bilayers for gene delivery. Chem Commun 2009, pp. 5100-5102.
Soderquist, RG, et al.; Release of Plasmid Dna-Encoding IL-10 from PLGA Microparticles Facilitates Long-Term Reversal of Neuropathic Pain Following a Single Intrathecal Administration. Pharmaceutical Research May 27, 2010: 841-854.
Sloane E, et al.; Immunological priming potentiates non-viral anti-inflammatory gene therapy treatment of neuropathic pain. Gene Therapy Jul. 2, 2009, 16:1210-1222.
Ashley, Carlee E. et al.; Delivery of Small Interfering RNA by Peptide-Targeted Mesoporous Silica Nanoparticle-Supported Supported Lipid Bilayers; ACS NANO Mar. 2012; vol. 6; pp. 2174-2188.
Dengler, Ellen C. et al.; Mesoporous silica-supported lipid bilayers (protocells) for DNA cargo delivery to the spinal cord; Journal of Controlled Release Mar. 2013; vol. 168; pp. 209-224.
Epler, Katharine et al.; Delivery of Ricin Toxin A-Chain by Peptide-Targeted mesoporous Silica Nanoparticle-Supported Lipid Bilayers; Advanced Healthcare Materials May 2012; vol. 1; pp. 348-353; DOI: 10, 1002/adhm.201200022. Epub Apr. 2, 2012.
Tarn, Derrick et al.; Mesoporous Silica Nanoparticle Nanocarriers: Biofunctionality and Biocompatibility; Accounts of Chemical Research Jun. 2, 2013; vol. 46; pp. 792-801.
Buranda, Tione et al.; Biomimetic Molecular Assemblies on Glass and Mesoporous Silica Microbeads for Biotechnology; Langmuir 2003; vol. 19, pp. 1654-1663.
Fishkis, M.; Self organization of short peptides and simple amphiphiles into membranes, Encapsulation of polynucleotide/polypeptide systems by membranes; Orig. Life Evol. Biosph. 2007; vol. 37; pp. 537-553.
Slowing, I. I. et al.; 2. Mesoporous silica nanoparticles; 5. Controlled release drug delivery; Advanced Drug Delivery Reviews 2008; vol. 60; pp. 1278-1288.

* cited by examiner

SEQUENCE LISTING

```
<160> NUMBER OF SEQ ID NOS: 3

<210> SEQ ID NO 1
<211> LENGTH: 23
<212> TYPE: PRT
<213> ORGANISM: Artificial Sequence
<220> FEATURE:
<223> OTHER INFORMATION: Peptide
```

```
<400> SEQUENCE: 1

Gly Leu Phe His Ala Ile Ala His Phe Ile His Gly Gly Trp His
1               5                   10                  15

Gly Leu Ile His Gly Trp Tyr Gly
                20

<210> SEQ ID NO 2
<211> LENGTH: 38
<212> TYPE: PRT
<213> ORGANISM: Artificial Sequence
<220> FEATURE:
<223> OTHER INFORMATION: Peptide

<400> SEQUENCE: 2

Asn Gln Ser Ser Asn Phe Gly Pro Met Lys Gly Gly Asn Phe Gly
1               5                   10                  15

Gly Arg Ser Ser Gly Pro Tyr Gly Gly Gly Gln Tyr Phe Ala
                20                  25                  30

Lys Pro Arg Asn Gln Gly Gly Tyr
                35

<210> SEQ ID NO 3
<211> LENGTH: 12
<212> TYPE: PRT
<213> ORGANISM: Artificial Sequence
<220> FEATURE:
<223> OTHER INFORMATION: Peptide

<400> SEQUENCE: 3

Ser Phe Ser Ile Ile Leu Thr Pro Ile Leu Pro Leu
1               5                   10
```

PROTOCELLS AND THEIR USE FOR TARGETED DELIVERY OF MULTICOMPONENT CARGOS TO CANCER CELLS

RELATED APPLICATIONS

This application claims priority to U.S. Provisional Patent Application Ser. No. 61/279,438, filed Oct. 21, 2009, and No. 61/306,123, filed Feb. 19, 2010, which are hereby incorporated by reference in their entirety.

GOVERNMENT RIGHTS

This invention was made with Government support under Contract No. PHS 2 PN2 EY016570B awarded by the National Institute of Health and Contract No. DE-AC04-94AL85000 awarded by the Department of Energy. The U.S. Government has certain rights in the invention.

BACKGROUND

Targeted delivery of drugs encapsulated within nanocarriers can potentially ameliorate a number of problems exhibited by conventional 'free' drugs, including poor solubility, limited stability, rapid clearing, and, in particular, lack of selectivity, which results in non-specific toxicity to normal cells and prevents the dose escalation necessary to eradicate diseased cells. Passive targeting schemes, which rely on the enhanced permeability of the tumor vasculature and decreased draining efficacy of tumor lymphatics to direct accumulation of nanocarriers at tumor sites (the so-called enhanced permeability and retention, or EPR effect), overcome many of these problems, but the lack of cell-specific interactions needed to induce nanocarrier internalization decreases therapeutic efficacy and can result in drug expulsion and induction of multiple drug resistance (MDR). Furthermore, not all tumors exhibit the EPR effect (Jain, (1994) Barriers to Drug-Delivery in Solid Tumors. *Scientific American* 271, 58-65), and passively-targeted nanocarriers are no more effective at treating blood cancers than free drugs (Sapra & Allen (2002), Internalizing Antibodies are Necessary for Improved Therapeutic Efficacy of Antibody-Targeted Liposomal Drugs. Cancer Res 62, 7190-7194). Selective targeting strategies employ ligands (e.g. peptides, monoclonal antibodies, aptamers, vitamins, etc.) that specifically interact with receptors expressed on the cell surface of interest to promote nanocarrier binding and internalization (Torchilin (2005), Recent Advances with Liposomes as Pharmaceutical Carriers. Nat. Rev Drug Discov 4, 145-160). This strategy requires that receptors are highly over-expressed by cancer cells ($10^4$-$10^5$ copies/cell) relative to normal cells in order to maximize selectivity and therapeutic efficacy. Additionally, multiple copies of a targeting ligand can be conjugated to the nanocarrier surface to promote multivalent binding effects, which result in enhanced affinity and more efficient drug delivery through the receptor-mediated internalization pathways that help circumvent MDR efflux mechanisms (Pastan, Hassan, FitzGerald, & Kreitman (2006), Immunotoxin Therapy of Cancer. Nat. Rev Cancer 6, 559-565).

Liposomes are one of the extensively studied classes of nanocarriers due to their biocompatibility and biodegradability, as well as the ease with which they can be surface-modified with targeting ligands and polyethylene glycol (PEG) to control functionality and improve circulation times. Liposomes are the first drug carrying nanoparticles to reach the clinic, but today, more than two decades after the regulatory approval of liposomal doxorubicin (Doxil) to treat AIDS-related Kaposi's sarcoma and other cancers (Gordon, et al. (2001) Recurrent Epithelial Ovarian Carcinoma: a Randomized Phase III Study of Pegylated Liposomal Doxorubicin Versus Topotecan. J Clin Oncol 19, 3312-3322), no targeted liposomes have cleared Phase I clinical trials.

The major challenge for liposomes and other targeted nanocarriers is to simultaneously achieve high targeting specificity and delivery efficiency, while avoiding non-specific binding and entrapment by the body's defences. Other desirable characteristics include a high capacity for disparate types of therapeutic and diagnostic agents, the ability to controllably release encapsulated cargo upon internalization within the target cell, stability, solubility, and lack of immunogenicity. In some cases, it is also desirable to direct the intracellular targeting of delivered cargo in order to maximize therapeutic efficacy.

Applicants have overcome these and other problems and provide effective materials and methods for synthesizing targeted nanocarriers.

SUMMARY

According to various embodiments, the present teachings include a protocell compound. The protocell compound can include a porous particle core; one or more cargo components disposed within the porous particle core; and a supported lipid bilayer (SLB) encasing the porous particle core and the one or more cargo components.

According to various embodiments, the present teachings also include a method of forming a protocell compound. In this method, the protocell compound can be formed by first fusing a first lipid bilayer to encase a porous particle core and one or more cargo components disposed within the porous particle core. A second lipid bilayer can then be used to electrostatically replace a portion of the first lipid bilayer to form a hybrid lipid bilayer encasing the porous particle core and the one or more cargo components. The first lipid bilayer and the second lipid bilayer can be oppositely-charged.

According to various embodiments, the present teachings further include a protocell compound. The protocell compound can include a lipid bilayer encasing a porous particle core and one or more cargo components disposed within the porous particle core. The protocell compound can also include a targeting ligand attached to the lipid bilayer for a selective binding to a target cell; and a shielding material attached to the lipid bilayer for reducing non-specific binding to the target cell and non-target cells.

According to various embodiments, the present teachings further include a method for delivering cargo components to a cancer cell. In this method, a protocell compound can be provided to include a lipid bilayer encasing a porous particle core; a plurality types of cargo components disposed within the porous particle core; a targeting ligand attached to the lipid bilayer for a selective binding to a target cell; a fusogenic ligand attached to the lipid bilayer; and a shielding material attached to the lipid bilayer to reduce non-specific binding to the target cell and non-target cell. Such protocell compound can then be mixed with the target cell such that the protocell compound can be selectively bound to the target cell and internalized in the target cell induced by the targeting ligand.

It is to be understood that both the foregoing general description and the following detailed description are exemplary and explanatory only and are not restrictive of the present teachings, as claimed.

BRIEF DESCRIPTION OF THE DRAWINGS

The accompanying drawings, which are incorporated in and constitute a part of this specification, illustrate several embodiments of the present teachings and together with the description, serve to explain the principles of the invention.

DESCRIPTION OF THE EMBODIMENTS

Reference will now be made in detail to exemplary embodiments of the present teachings, examples of which are illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments in which the present teachings may be practiced. These embodiments are described in sufficient detail to enable those skilled in the art to practice the present teachings and it is to be understood that other embodiments may be utilized and that changes may be made without departing from the scope of the present teachings. The following description is, therefore, merely exemplary.

Various embodiments provide materials and methods for protocells used for targeted delivery of cargo components to cancer cells. In one embodiment, liposomes can be fused with porous particles to form a protocell. The protocell can thus have a supported lipid bilayer (SLB) on the porous particle surface. The SLB can be modified with one or more copies of targeting ligands or other ligands for the targeted delivery of one or more cargo components that are loaded within the protocell to a target cell of, e.g., a type of cancer. In embodiments, shielding materials can be conjugated to the surface of the SLB to reduce undesired non-specific binding. As compared to conventional targeted delivery of therapeutics and diagnostics using liposomes, use of protocells can improve upon stability and selectivity and can enable the targeted delivery and controlled release of high concentrations of cargo components.

Figure 1A:
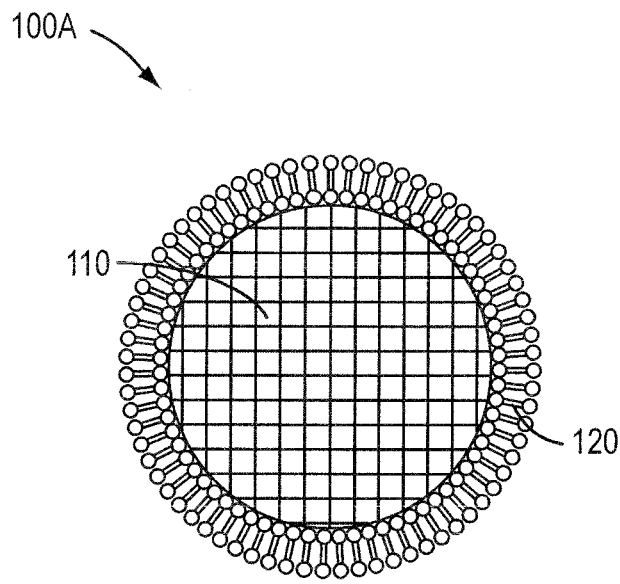
FIG. 1A depicts an exemplary protocell in accordance with various embodiments of the present teachings.

As used herein, the term "protocell" refers to a nanostructure having a porous particle core 110, which is interchangeable with the term "porous particle" as used herein, and a lipid bilayer 120 encasing (or surrounding or enveloping) the porous particle core 110, an example of which is shown in FIG. 1A. The protocell can mimic bioactive cells (or real cells) that have a lipid bilayer membrane.

As used herein, the term "lipid" refers to conventional lipids, phospholipids, etc. As used herein, the term "lipid bilayer" refers to any double layer of oriented amphipathic lipid molecules in which the hydrocarbon tails face inward to form a continuous non-polar phase. The term "lipid bilayer" also includes a hybrid lipid bilayer.

As used herein, the term "hybrid lipid bilayer" refers to a lipid bilayer that is derived from more than one source, either through a mixing process before formation, or post bilayer fusion. For example, the hybrid lipid bilayer can include a first lipid bilayer having a portion exchanged by a second lipid bilayer, e.g., to form a SLB on a porous particle core. Such lipid exchange processes can include, e.g., electrostatically-mediated liposome fusion of the first and the second lipid bilayers, as will be described later in great detail, and can be used to control surface charge, cargo containment, and delivery of protocell compounds.

As used herein, the term "liposome" refers to an aqueous compartment enclosed by a lipid bilayer, as being conventionally defined (Stryer (1981) Biochemistry, 2d Edition, W. H. Freeman & Co., p. 213).

Compared with the lipid bilayer defined in a protocell, the lipid bilayer in a liposome can be referred to as an "unsupported lipid bilayer" and the liposome itself can be referred to as an "empty liposome". The lipid bilayer in a protocell can be referred to as a "supported lipid bilayer" or "SLB," because the lipid bilayer in protocells is located on and supported by a porous particle core. As disclosed herein, the lipid bilayer can have a thickness, e.g., ranging from about 1 nm to about 200 nm, or from about 3 nm to about 50 nm, or from about 3 nm to about 5 nm.

As used herein, the term "protocell compound" refers to a protocell loaded with one or more cargo components in the porous particle core part, e.g., on pore surfaces and/or particle surfaces of the porous particle, of the protocell.

Cargo components can include, but are not limited to, drugs, proteins, peptides, antibodies, nucleic acids (e.g., DNA or RNA), fluorescent dyes, inorganic nanoparticles (e.g., gold nanoparticles, magnetic nanoparticles, or quantum dots), chemotherapeutic drugs, anti-cancer drugs, etc. for applications in biomedical diagnostics, imaging, disease treatment, and/or anti-bacterial applications. In embodiments, the cargo components can be loaded in an amount of about 1% to about 50%, by weight or by mole of the porous particle pore, although other loading percentages can also be used.

As used herein, the term "net positive charge" or "net positive surface charge" means that the overall charge on the surface of the protocell or protocell compound is positive. For example, the surface of protocells or protocell compounds can have a net positive charge, when a positively-charged lipid bilayer is used; or when a hybrid lipid bilayer is used having a positively-charged lipid bilayer and a negatively-charged lipid bilayer, but the positively-charged lipid bilayer is present in an amount that is more than the negatively-charged lipid bilayer to provide an overall positive charge on surface of the resulting protocells or protocell compounds.

As used herein, the term "selective targeting" or "specific binding" refers to use of targeting ligands on the surface of protocells or protocell compounds, in particular, on the surface of the lipid bilayer of the protocells or protocell compounds, wherein the ligands interact specifically/selectively with receptors or other biomolecular components expressed on the cell surface of interest. The targeting ligands can include such molecules and/or materials as peptides, monoclonal antibodies, aptamers, vitamins, etc.

The protocell with targeting ligands can be referred to as a "targeted protocell" and the protocell compound with targeting ligands can be referred to as a "targeted protocell compound." The cell of interest can be referred to as a "target cell," as opposed to a "normal cell".

As used herein, the term "shielding material" refers to molecules or polymers that are present on the surface of protocells or protocell compounds, in particular, on the surface of the lipid bilayer of the protocells or protocell compounds, to reduce non-specific interactions with or binding to non-target proteins, cells, and/or tissues, such as serum proteins and macrophages of the reticuloendothelial system. The shielding materials can be hydrophilic. The shielding materials can include, but are not limited to, polyethylene glycol (PEG), cholesterol, and/or combinations thereof.

Referring back to FIG. 1A, the porous particle core 110 can be made of a material primarily composed of polystyrene, silica, alumina, titania, zirconia, etc. The porous particle core 110 can have an average particle size ranging from about 30 nm to about 3000 nm, or about 200 nm or less, such as about 100 nm or 150 nm. In one embodiment, particles larger than about 200 nm in diameter can be removed for specific applications via differential centrifugation or size-exclusion chromatography as known to one of ordinary skill in the art. The porous particle core 110 can be in various forms including, e.g., spherical, cylindrical, oblong or other three-dimensional (3-D) forms.

In embodiments, the porous particle core 110 can have a controllable average pore size ranging from about 2 nm to about 30 nm, an average porosity ranging from about 25% to about 75%, and a surface area ranging from about 100 to about 2500 $m^2/g$, e.g., about 1000 $m^2/g$ or more. Due to the high surface area, the porous particle core, such as a porous nanoparticle silica core, can confer a higher cargo capacity to protocells when compared to liposomes, which do not have a porous particle core. In embodiments, the porous particle core 110 can have, e.g., isotropic wormlike nanoporosity. In embodiments, the sizes, shapes, pore features, and surface properties of the porous particle core 110 are not limited.

In one embodiment, the porous silica particles can be formed by, for example, mixing water, HCl, ethanol, cetyltrimethylamonium bromide (CTAB), and tetraethyl orthosilicate (TEOS), as disclosed in a related International Patent Application No. PCT/US10/20096, entitled "Porous Nanoparticle Supported Lipid Bilayer Nanostructures," which is hereby incorporated by reference in its entirety.

In embodiments, the porous particle 110 (e.g., porous silica particles) can have a controllable surface charge. For example, the surface charge of porous silica particles can switch from negative to positive at neutral pH values by using amine-modified silane precursors and by controlling the percentage of amine groups within the porous silica particles. For example, the porous silica particles can have an amine-containing composition, and the amine-modified silane precursors can include, for example,

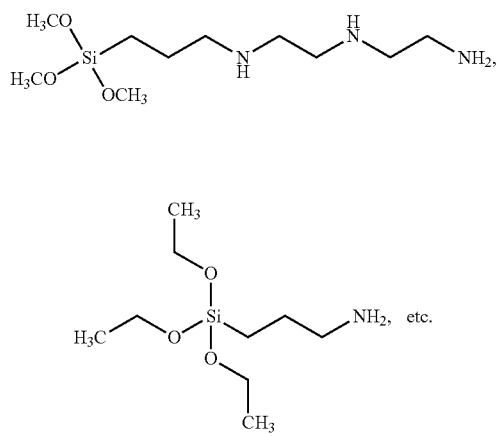

For example, the exemplary porous silica particles can be cationic porous silica particles by using the above-mentioned amine-modified silane precursor of 3-2[2-(2-aminoethylamino)ethylamino]propyltrimethoxysilane (AEPTMS) mixed with TEOS and CTAB, wherein from 0 wt % to about 30 wt %, such as about 15 wt %, of the amine-modified silane precursor can be used.

One of ordinary skill in the art would understand that cargo components can be adsorbed onto oppositely-charged porous particle cores due to electrostatic interactions. For example, negatively-charged cargo components, such as the dye calcein or DNA, can be adsorbed into the pores of positively-charged porous silica particles in high concentrations. However, when the porous particles 110 carrying the oppositely-charged cargo components are dispersed in a saline solution, e.g., a buffer solution or a cell culture medium, the oppositely-charged cargo components can be displaced by the ions in the saline solution.

To provide stability of components loaded on and within the porous particle core 110, the lipid bilayer 120 can be fused onto the porous particle core to form the protocell 100A. The lipid bilayer 120 can include a phospholipid including, e.g., 1,2-dioleoyl-sn-olycero-3-[phospho-L-serine] (DOPS), dioleoyl-3-trimethylammonium-propane (DOTAP), 1,2-dioleoyl-sn-glycero-3-phosphocholine (DOPC), dipalmitoylphosphatidylcholine (DPPC), 1,2-dioleoyl-sn-glycero-3-phosphoethanolamine (DOPE), or DPPE, and/or a combination thereof. The protocells can therefore include DOPC protocells, DOTAP protocells, and/or DOPS protocells. In embodiments, the lipid bilayer 120 can be negatively-charged (e.g., DOPS), positively-charged (e.g., DOTAP), and/or zwitterionic (e.g., DOPC).

Figure 1B:
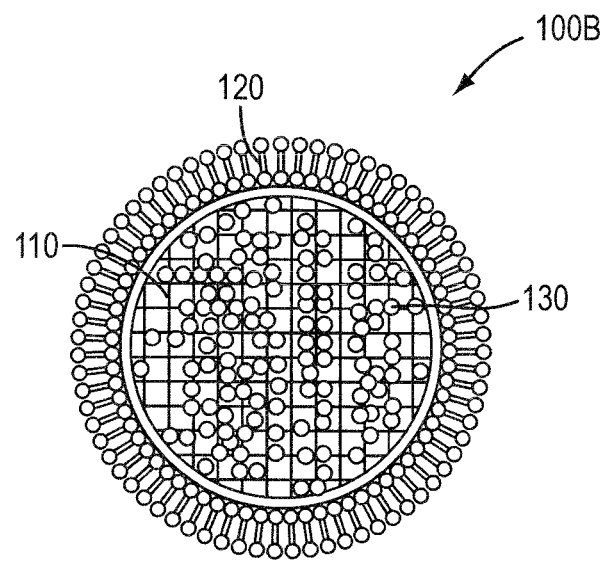
FIGS. 1B-1D depict various exemplary protocell compounds in accordance with various embodiments of the present teachings.

In FIG. 1B, the protocell compound 100B can include a lipid bilayer 120 encasing a porous particle core 110 wherein one or more cargo components 130 including e.g., multicomponent cargo components, can be disposed on the particle surfaces or pore surfaces of the porous particle core 110.

The protocell compound 100B can be formed by mixing the cargo components 130 and the porous particle 110 with liposomes or lipids, followed by fusing the lipid bilayer 120 on the porous particle 110 and synergistically loading the cargo components 130 into one or more pores of the porous particle 110 to form the protocell compound 1008, which is also similarly described in the above-mentioned International Patent Application No. PCT/US10/20096.

Figure 1C:
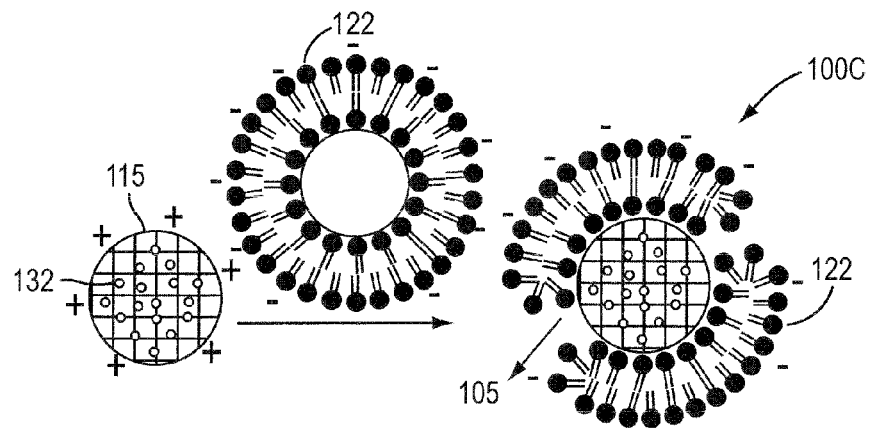

FIG. 1C depicts an exemplary protocell compound 100C. Positively-charged porous particles 115 can be fused with negatively-charged lipid bilayers 122, such as a DOPS lipid bilayer, wherein the positively-charged porous particles 115 can absorb negatively-charged cargo components 132 (e.g., calcein or DNA or siRNA). The use of a lipid bilayer to encase the porous particle core loaded with cargo components can provide pore sealing, which reduces or avoids the cargo displacement. However, the negatively-charged lipid bilayer 122 can be electrostatically repelled by target cells, which often have a negatively-charged cell surface. Additionally, defects 150 can be formed when anionic (or negatively-charged) lipid bilayers 122 (e.g., DOPS) are fused with cationic (or positively-charged) porous particle cores 115.

Figure 1D:
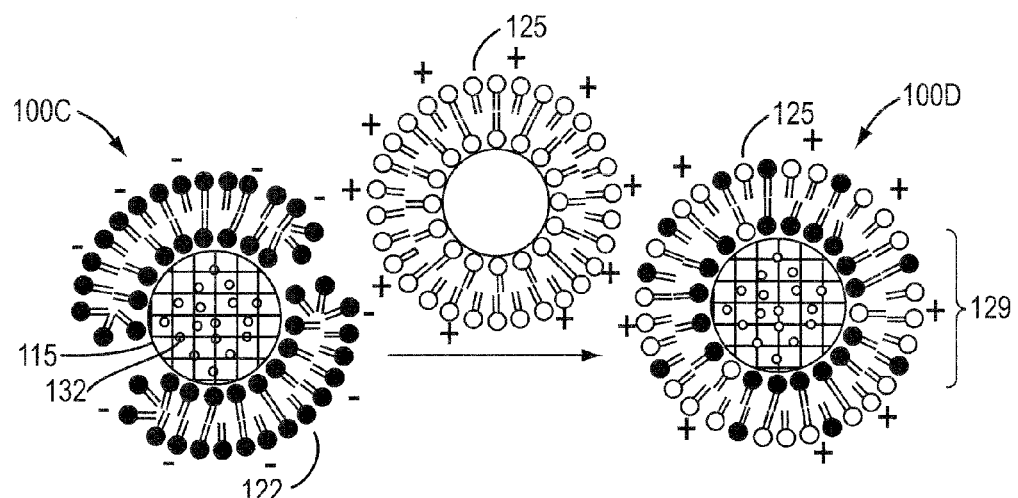

FIG. 1D depicts a protocell compound 100D having a net positive surface charge in accordance with various embodiments of the present teachings. For example, an oppositely-charged, e.g., positively-charged lipid bilayer 125, can be mixed with negatively-charged lipid bilayer 122 of the protocell compound 100C in FIG. 1C. A portion of the negatively-charged lipid bilayer 122 can then be replaced or exchanged by the positively-charged lipid bilayer 125 to form a hybrid lipid bilayer 129 with a net positive charge encasing the positively-charged porous particle 115 to form a protocell compound 100D. The net positive charge of the protocell compounds 100D (or related protocells) can then provide electrostatic interaction with a target cell that is negatively-charged. It is discovered that the mixing or exchanging process of oppositely-charged lipid bilayers (see 122 and 125 in FIGS. 1C-1D) can be repeated as desired, provided that the positively-charged lipid bilayer 125 is added as a last step for forming the protocell compound 100D. A net positive surface charge can be generated and defects can be reduced.

In embodiments, the surface charge of the protocells or protocell compounds can be made positive or negative, depending on the charge type of the lastly-added liposome. By adding different concentrations of positively-charged, e.g., DOTAP, liposomes to supported negatively-charged, e.g., DOPS bilayers, the surface charge of the resulting supported bilayers can be systematically controlled. In embodiments, the lipid bilayer 129 in FIG. 1D can be formed by one type of lipids having positive charges or various types of lipids all having positive charges to provide a net positive surface charge for the protocell or protocell compounds.

In this manner, the lipid bilayer fused to the porous particle core can create a cell-like protocell structure and can prevent premature cargo release in a manner similar to the cell membrane. Additionally, the lipid bilayer can remain fluid and functional moieties such as targeting/fusogenic ligands and/or shielding materials can be attached to the surface to promote targeting and enhanced circulation. Further, the fusion of a lipid bilayer to the porous particle core can provide substrate-membrane adhesion energy, which suppresses large-scale bilayer fluctuations and results in greater stability of protocells. Even further, the porous particle as a support can result in enhanced lateral bilayer fluidity as compared with that of empty liposomes. For example, a significant reduction (by about 6° C.) of the lipid bilayer (membrane) fluidization temperature shows that physical constraints occur at the interface between the lipid bilayer 120 and the porous particle core 110, 115.

In one embodiment, the underlying 3D porosity and corresponding periodic roughness of the surface of the porous particle core, which can include nanoscopic patches of silica and water, generates gradients of local adhesion in nanoscale, curvature, and lateral tension of the supported lipid bilayer 120, together contributing to enhancing long-range, in-plane fluidity without appreciably changing its average packing density. Meanwhile, the porous particle core can suppress all but nanoscopic out-of-plane bilayer fluctuations.

As used herein, the term "fluidity" refers to the mobility of the lipid components of the supported lipid bilayer (SLB) fused to the porous particle core. The term "fluidity" can be put into numerical terms by, for instance, measuring the diffusion coefficient of lipids using techniques such as fluorescence recovery after photobleaching and by determining that the protocell compound is at a temperature above the melting transition temperature, $T_m$, of the lipid bilayer. The fusion of the lipid bilayer onto the nanoporous particle core can reduce the $T_m$ of the SLB corresponding to increased fluidity as compared with an unsupported lipid bilayer and/or the lipid bilayer that is not formed by fusion, which is unique and unanticipated by practitioner of the art.

In embodiments, the disclosed protocells and/or the protocell compounds can provide biocompatibility, and their surfaces can be modified with desired ligands and/or shielding materials to effect specific delivery and enhanced targeting efficacy with a minimal number of ligands/materials and to optimize the combination of specific and non-specific binding and minimize dosage and immune response.

Figure 2A:
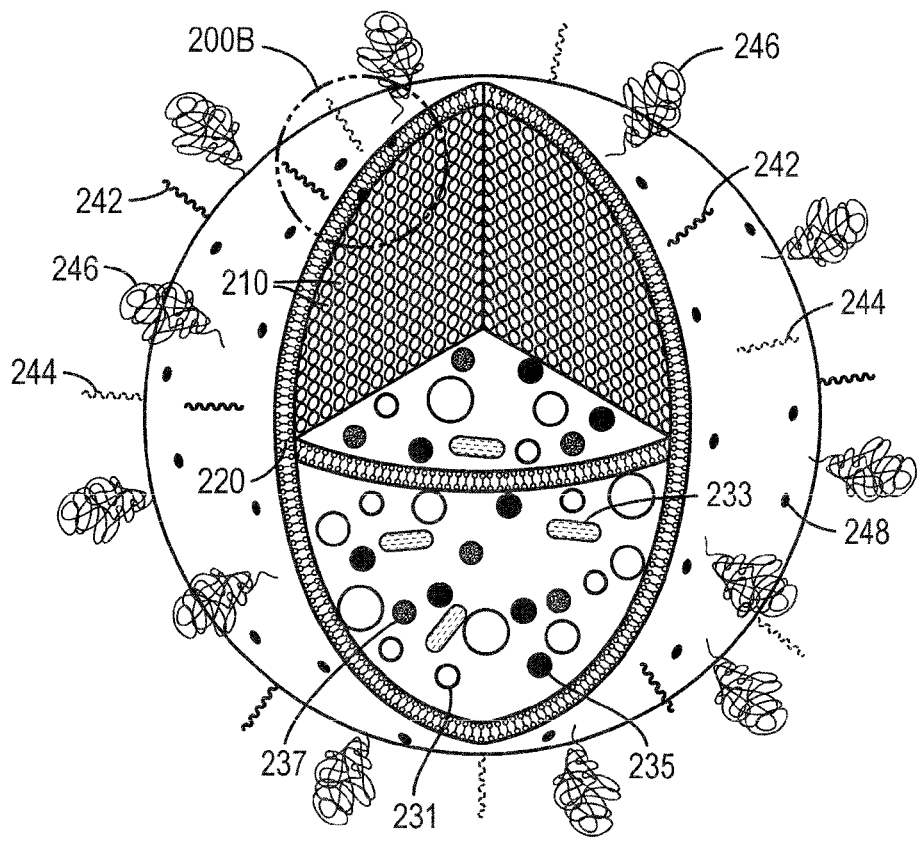
FIGS. 2A-2C depict an exemplary targeted protocell compound including ligands and/or shielding materials in accordance with various embodiments of the present teachings.
Figure 2B:
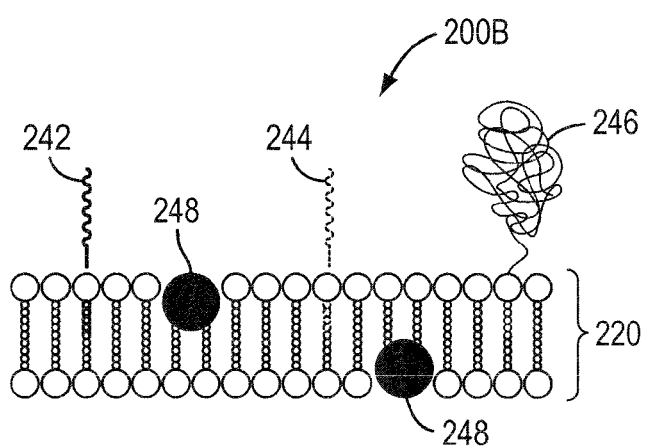
Figure 2C:
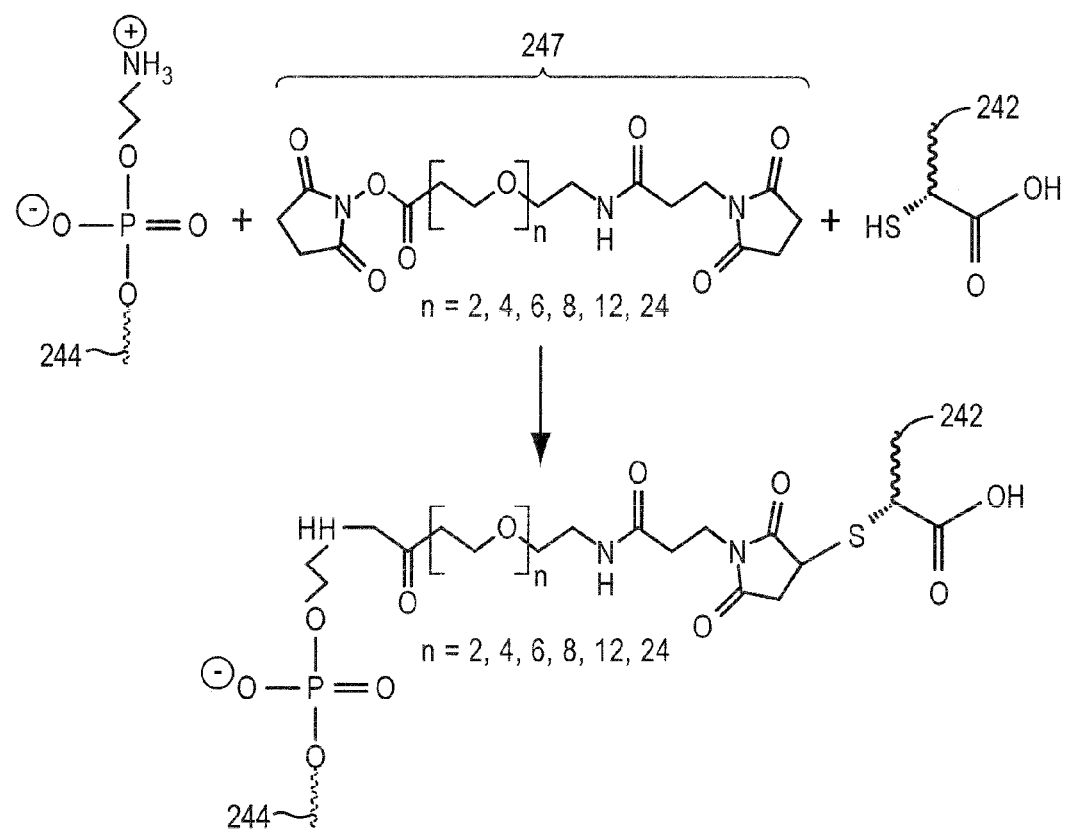

FIGS. 2A-2C depict an exemplary protocell compound that is surface modified, e.g., with targeting ligands for a specific target and/or shielding materials for reducing undesired non-specific binding in accordance with various embodiments of the present teachings.

As shown in FIG. 2A, the protocell compound 200A can include a lipid bilayer 220 encasing the porous particle core 210, wherein various cargo components (see 231, 233, 235, 237) can be loaded within the porous particle core 210.

The cargo components can include one or more disparate types of, e.g., therapeutic or diagnostic agents loaded within the porous particle core 210, such as a nanoporous silica core. As shown in FIG. 2A, exemplary cargo components can include, e.g., quantum dots 231, siRNA 233, nanoparticles 235, diphtheria toxin 237, doxorubicin, 5-fluorouracil, cisplatin, or other cargo components as disclosed herein.

An exemplary lipid bilayer 220 can include one or more of DOPE, DPPE, DOPC, DPPC, DOTAP, etc. In embodiments, the lipid bilayer 220 can have a net positive surface charge. In embodiments, 1,2-dioleoyl-sn-glycero-3-phosphoethanolamine (DOPE) can be incorporated within the lipid bilayer to facilitate the attachment or conjugation of targeting ligands 242, such as small peptide sequences, to achieve receptor-mediated cell targeting.

Various targeting ligands 242 can be attached to and displayed on the surface of the lipid bilayer 220 for selective targeting or specific binding of the protocell compound 200A to target cells. Exemplary targeting ligands 242 can include small peptide sequences such as targeting peptides, antibodies, vitamins, aptamers, or other compounds for achieving receptor-mediated cell targeting. The targeting peptides 242 can include, for example, SP94 peptides of $H_2N$-SFSIILT-PILPL-COOH, identified via filamentous phage display to have an affinity for receptor(s) expressed by human liver cancer (hepatocellular carcinoma, or HCC).

In embodiments, fusogenic ligands 244, e.g., fusogenic peptides can also be displayed on the surface of the lipid bilayer 220. The fusogenic peptides 224 can include, for example, a histidine-rich fusogenic peptide (H5WYG: $H_2N$-GLFHAIAHFIHGGWHGWYG-COOH SEQUENCE ID NO. 1)) (Midoux et al., (1998) Membrane Permeabilization and Efficient Gene Transfer by a Peptide Containing several Histidines. Bioconjugate Chemistry 9, 260-267) that promotes endosomal escape without affecting the integrity of the cell membrane.

The targeting ligands 242 and/or the fusogenic ligands 244 can be attached to the SLB 220 by a chemical reaction, e.g., by a cross-linker 247. The cross-linker 247 can be, e.g., a heterobifunctional cross-linker with a polyethylene glycol (PEG) spacer arm. In embodiments, the cross-linker 247 can include, for example, 1-ethyl-3-[3-dimethylaminopropyl] carbodiimide hydrochloride (EDC), succinimidyl-6-[β-maleimidopropionamido]hexanoate (SMPH), succinimidyl-([N-maleimidopropionamido]-8-ethyleneglycol) ester (SM(PEG)$_8$), etc. As exemplarily shown in FIG. 2C, the cross-linker 247 can cross-link both targeting peptides 242 and fusogenic peptides 244 onto the surface of the SLB 220.

Attaching or displaying multiple copies of the targeting ligands on the SLB surface can provide collective, multivalent binding effects for enhanced affinity and more efficient cargo delivery through receptor-mediated internalization pathways. In embodiments, from 1 to about 2048 copies of targeting peptides 242, or from 0.002 wt % to about 5.0 wt % targeting peptides 242 can be attached to and displayed on the SLB 220. For example, about 2048 copies of the SP94 targeting peptide 242, or about 5 wt % of the SP94 targeting peptide 242 can be displayed on the SLB 220 to effect specific targeting of Hep3B, an exemplary type of the target cell (HCC). In embodiments, from about 6 to about 2048 copies of fusogenic peptides 244 can be attached to or displayed on a SLB 220.

The SLB 220 can be modified by various shielding materials including, e.g., polymers 246, such as PEG, cholesterol 248, etc. as shown in FIGS. 2A-2B. For example, PEG-2000-PE can be used as shielding materials to reduce or avoid non-specific binding of the protocell compounds 200A.

Figure 3A:
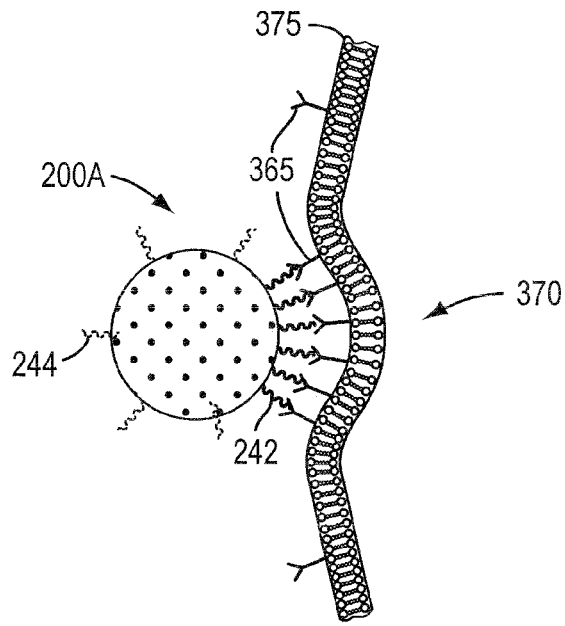
FIG. 3A depicts a targeted binding process of an exemplary targeted protocell compound in accordance with various embodiments of the present teachings.

FIG. 3A depicts an exemplary selective targeting process of the disclosed protocell compound in accordance with various embodiments of the present teachings.

Protocells modified with targeting ligands, e.g., SP94, can also bind non-specifically to normal cells, e.g. hepatocytes, immune cells, etc., which can be a function of the charge and fluidity of lipids employed in the SLB and the degree to which the SLB is modified with shielding materials such as PEG.

For example, employing zwitterionic lipids, such as DOPC and/or DPPC, or hybrid lipids such as the protocell compound 100D of FIG. 1D, in the SLB can minimize non-specific binding and maximize specific binding, while lipids with a positive charge (DOTAP) or negative charge (DOPS) can increase undesired non-specific binding of protocells to normal cells. Incorporating the exemplary cholesterol or PEG-2000-PE into the SLB can further reduce the non-specific binding of, e.g., DOPC and/or DPPC protocells.

In a specific embodiment, the protocell 200A can have cholesterol of 0 to about 50 wt %, or about 5 wt % to about 30 wt %, such as about 30 wt %; PEG 2000 or other PEGylated lipid of 0 to about 50 wt %, or about 1 wt % to about 30 wt %, such as about 5 wt %; phosphatidylethanolamine (PE) of about 1 wt % to about 10 wt %; and/or DOPE of 0 to about 10 wt %, such as about 5 wt %, and the remainder DOPC ($T_m$=−20° C.) or DPPC ($T_m$=41° C.). Using a heterobifunctional crosslinker with a PEG (n=8) spacer, SP94 peptides having an affinity for receptor(s) expressed by human HCC can be covalently attached to DOPE head groups with desirable concentrations ranging from 0.002 to 5.0 wt %, corresponding, on average, from about 1 to 2048 peptides per particle.

In embodiments, the SLB composition can be used to promote selective targeting of the protocell or the protocell compounds to target cells but not to other cells such as normal cells. For example, protocells possessing a fluid SLB such as DOPC are able to selectively target HCC at low SP94 densities, which is in contrast to a non-fluid or solid SLB, such as the DPPC SLB.

The binding affinity can be measured by $K_d$ values, a dissociation constant that is inversely related to binding affinity. For example, targeted DOPC or DPPC protocells can have a high specific affinity with $K_d$<1 nM for HCC and, over the range of 6 to 2048 peptides per particle, can have $K_d$ values that are consistently low (e.g., 0.94-0.08 nM) and relatively independent of peptide density. The $K_d$ values of SP94-targeted protocells can be precisely modulated by incorporating various amounts of fluid and non-fluid lipids into the SLB.

In one example, the differential binding affinity for HCC cancer cells over normal cells such as hepatocytes and other negative control cells, including human endothelial cells (HUVECs) and immune cells (PBMCs and B- and T-lymphocytes) can be about $10^4$ or greater. In embodiments, the differential binding affinity, i.e., the selectivity for the target cell (e.g., HCC) over other cells can be translated into differential internalization efficiency. As shown in FIG. 3B, the protocell compounds 200A that are selectively targeted to the receptor 365 can be selectively internalized into the corresponding target cell 370. In embodiments, protocells having an average particle size ranging from about 30 nm to about 300 nm can be internalized by the target cell (Hep3B) at 37° C.

Following the high affinity surface binding of targeting ligands 242 to the receptor 365 shown in FIG. 3A, FIG. 3B depicts receptor-mediated endocytosis or internalization to deliver multicomponent cargo components that are previously loaded in the porous particle core 210 of the protocell compound 200A. As shown in FIG. 2A, cargo components 242 including, but not limited to, quantum dots 231, siRNA 233, nanoparticles 235, diphtheria toxin 237 and other protein toxins, chemotherapeutic agents, e.g. doxorubicin and other drugs, etc. can all be simultaneously and uniformly loaded within a porous particle core that is then fused with a fluid lipid bilayer 220, e.g., by a DOPC liposome.

In FIG. 3B, the protocell compound 200A including the porous particle core 210 and cargo components 242 can be endocytosed by the target cell 370, e.g., by Hep3B cells. A saturating intracellular concentration, e.g., about 500 protocell compounds per Hep3B cell can be reached within, e.g. 2 hours.

Endosome acidification can destabilize the SLB 220 of the internalized protocell compound 200A, thereby enabling encapsulated cargo components 230 to diffuse out of the porous particle core 210 and into the cytosol 390. Additionally, protonation of imidazole moieties ($pK_a$=6.0) in the fusogenic peptide 244 can initiate osmotic swelling and membrane destabilization of endosomes (see 380 in FIG. 3B) via the 'proton sponge' mechanism. In an exemplary embodiment, approximately 4 hours after endocytosis, the exemplary cargo components 230 along with the lipid and silica moieties of the protocell can be distributed throughout the cytosol of Hep3B cells.

Figure 3C:
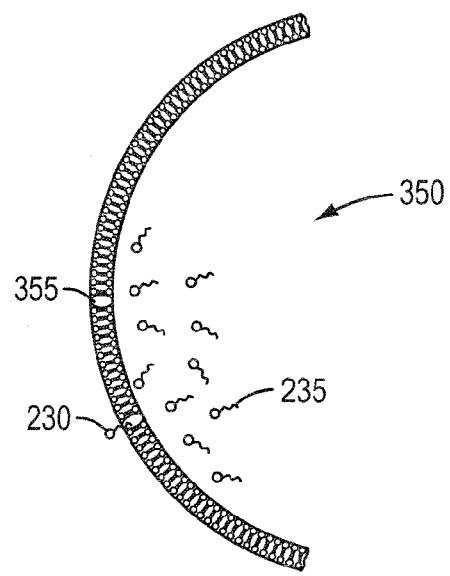
FIGS. 3B-3C depict exemplary cell internalization processes of the targeted protocell compound in FIG. 3A in accordance with various embodiments of the present teachings.
Figure 3B:
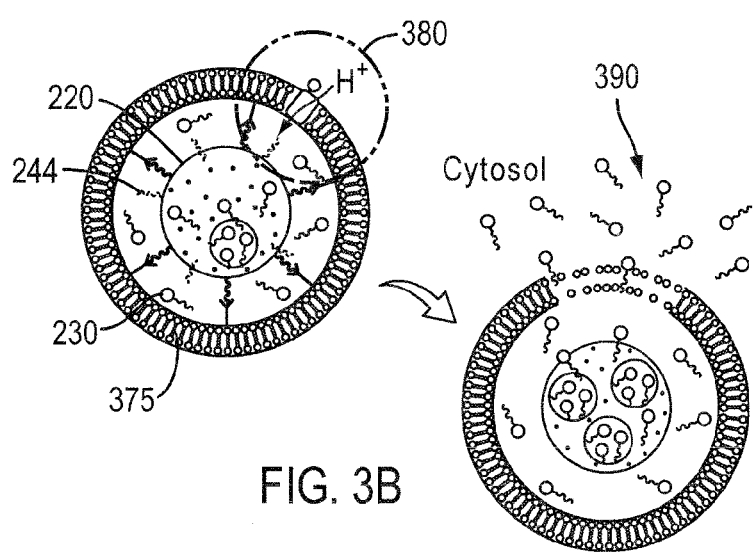

In FIG. 3C, cargo components 230 can be modified with a nuclear localization sequence, NLS 235 including e.g., the M9 domain of heterogeneous nuclear ribonucleoprotein A1 having a sequence of $H_2N$-NQSSNFGPMKGGNFGGRSS-GPYGGGGQYFAKPRNQGGY-COOH (SEQUENCE ID NO. 2), to promote transport of NLS-modified cargo components 230 through the nuclear pore complex 355 into the cell nucleus 350. Other unmodified cargo components can remain in the cytosol 380. For example, NLS-modified calcein and dsDNA can be concentrated within the Hep3B nucleus, whereas the remaining cargo components remain concentrated in the cytosol.

The disclosed protocell compounds and their binding and internalizing processes can thus provide high targeting specificity and high cytotoxicity to target cells, but with low collateral damage to normal cells.

EXAMPLES

Example 1

Electrostatic Interaction: Cargo Components Vs. Porous

Particle

Calcein, a negatively-charged and membrane-impermeable fluorophore, was used as an exemplary cargo component or surrogate representing a class of drug compounds. When calcein was mixed with negatively-charged silica nanoparticles and the mixture thereof was centrifuged, the dye remained in the supernatant and particles were colorless, indicating that negatively-charged calcein was excluded from negatively-charged silica mesopores.

An amine-modified silane, AEPTMS, was then introduced into the silica framework to prepare cationic mesoporous silica cores with about 2-nm diameter pores prepared by aerosol-assisted self-assembly using tetraethylorthosilicate (TEOS) plus 10 mol % AEPTMS as silica precursors and CTAB as a structure-directing agent. When the cationic silica particles were dispersed in water at about 25 mg/mL in the presence of about 1 mM calcein, greater than 99% of the calcein (determined by fluorimetry) was adsorbed into the pores, resulting in a 2.5 wt % loading relative to silica, while with saturated calcein, loading can reach 24.2% by weight.

Example 2

Displacement of Cargo Components in Cell Culture Medium

The calcein-loaded cationic silica particles of Example 1 were delivered to Chinese hamster ovary (CHO) cells. As a result, no calcein uptake was observed because no green fluorescence was observed associated with the CHO cells. This was also confirmed by flow cytometry studies (not shown) where the fluorescence histogram of cells incubated with the calcein-loaded particles was similar to that of cells incubated with free calcein, due to displacement of calcein by molecules/ions in the cell culture media. This was confirmed by fluorescence measurement of the cell culture medium, e.g., the F-12K medium, where calcein was found to be quantitatively displaced into the medium after particle centrifugation. Further experiments showed that small polyvalent anions, such as phosphate, sulfate, and carbonate, as well as chloride were effective in promoting calcein displacement.

Example 3

Lipids, Shielding Polymers, and Cargo Components

DOTAP: 1,2-Dioleoyl-3-Trimethylammonium-Propane (Chloride Salt)

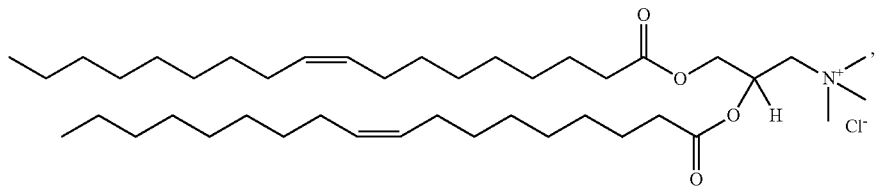 [SMILES: CCCCCCCC/C=C\CCCCCCCC(=O)OCC(C[N+](C)(C)C)OC(=O)CCCCCCC/C=C\CCCCCCCC ; [Cl-]]

DOPC: 1,2-Dioleoyl-sn-Glycero-3-Phosphocholine

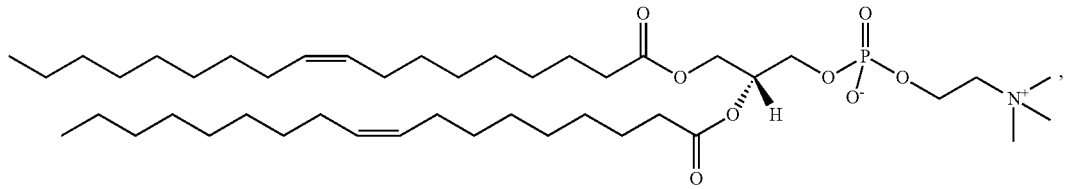 [SMILES: CCCCCCCC/C=C\CCCCCCCC(=O)OC[C@H](COP(=O)([O-])OCC[N+](C)(C)C)OC(=O)CCCCCCC/C=C\CCCCCCCC]

DPPC: dipalmitoylphosphatidylcholine

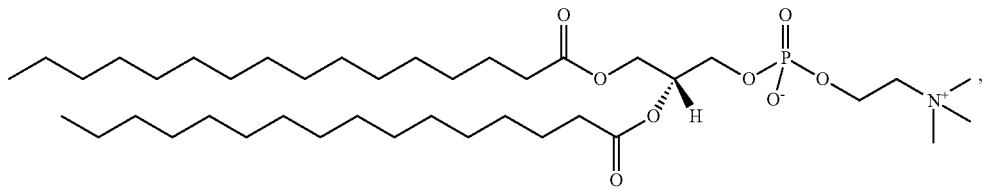 [SMILES: CCCCCCCCCCCCCCCC(=O)OC[C@H](COP(=O)([O-])OCC[N+](C)(C)C)OC(=O)CCCCCCCCCCCCCCC]

DOPS: 1,2-Dioleoyl-sn-Glycero-3-[Phospho-L-Serine] (Sodium Salt)

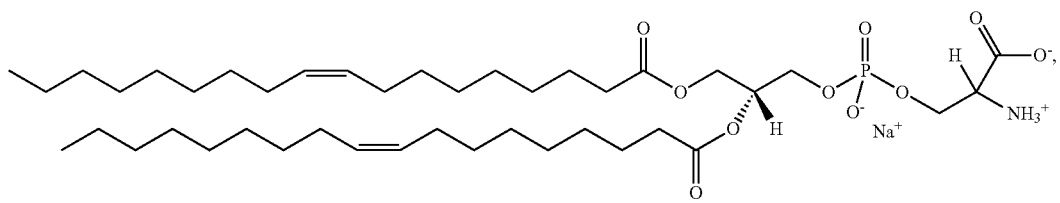

DOPE: 1,2-dioleoyl-sn-glycero-3-phosphoethanolamine

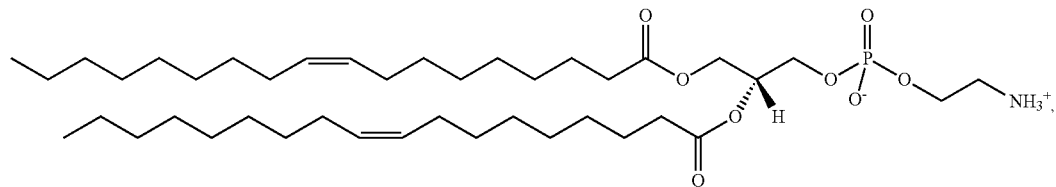

PEG-2000-PE (18:1):

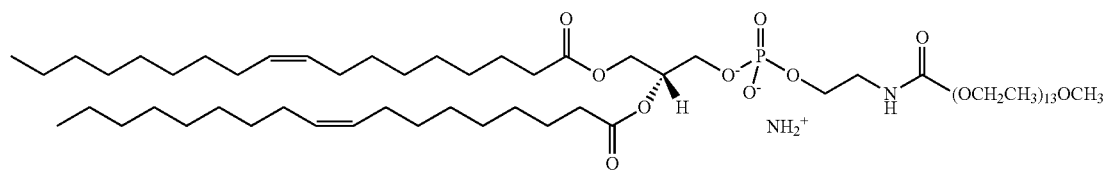

Cholesterol

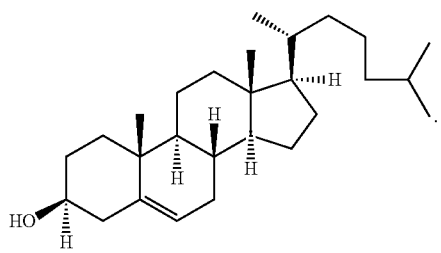

Doxorubicin

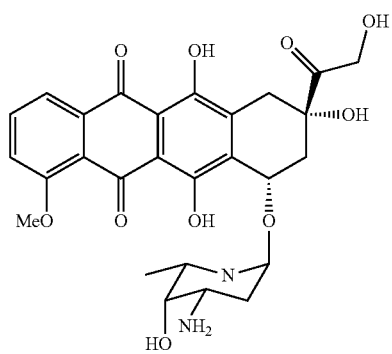 [SMILES: COc1cccc2c1C(=O)c1c(O)c3c(c(O)c1C2=O)C[C@@](O)(C(=O)CO)C[C@@H]3OC1CC(N)C(O)C(C)N1]

5-Fluorouracil

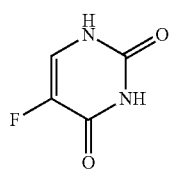

Cisplatin

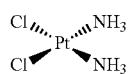

Example 4

Hybrid Lipid Bilayer for Sealing Calcein

Positively-charged silica nanoparticles were readily fused with anionic 1,2-dioleoyl-sn-glycero-3-[phosphor-L-serine] (DOPS) liposomes. After the DOPS bilayer was applied, the premature release of loaded calcein was reduced by about 55%. However, the cellular uptake of loaded calcein was slightly improved, which was attributed to the negative charge of the supported DOPS bilayer being repelled by the negatively-charged cell surface.

Free cationic (DOTAP) liposomes were mixed with anionic DOPS protocells to provide a net positive charge on the resulting protocell surface. Sealing and delivery of cargo components can be improved, e.g., by reducing the premature calcein release by about 75% from CHO cells.

Example 5

Hybrid Lipid Bilayer for Sealing Doxorubicin

The delivery of doxorubicin, a red-fluorescent chemotherapeutic drug was tested. Positively-charged doxorubicin was absorbed by pure anionic mesoporous silica particles (e.g., about 4 wt % loading relative to silica). With doxorubicin-loaded naked silica particles, a relatively uniform red fluorescence was observed within the cells, similar to that resulting from incubation with free doxorubicin.

Cationic protocell compounds were constructed by successive addition of three liposomes (e.g., DOTAP/DOPS/DOTAP) to form a hybrid lipid bilayer on the doxorubicin-loaded silica particles. A very bright punctuated pattern was produced within CHO cells, indicating that at least a fraction of the doxorubicin was delivered by the cationic protocells. Flow cytometry results also showed higher doxorubicin fluorescence when the cells were mixed with protocells.

When the medium supernatant fluorescence data were compared, the emission from the cationic compounds was only about one-third of that from the doxorubicin-loaded naked silica, meaning that the SLB was effective in maintaining the cargo within the protocell prior to entry into a cell. Drug toxicity was reduced by using the protocell to avoid drug leakage prior to the protocells entering the cell, demonstrating the efficacy of the protocell to contain cargo. For example, DOTAP protocells yielded more than 98% cell viability.

Example 6

Lipid Exchange Mechanism for Forming Hybrid Lipid Bilayers

After a supported lipid bilayer (SLB) is mixed with oppositely-charged free liposomes and centrifuged, the zeta potentials of both silica nanoparticle-supported bilayers (protocells) and the empty liposomes of the supernatant were monitored. The pure empty DOPS and DOTAP liposomes had potentials of about 43 and 46 mV, respectively.

However, after the first fusion step, the absolute values of the potentials for both the protocells and liposomes were less than those of free liposomes, indicating that the surface layer included a lipid mixture, or a hybrid lipid bilayer. That is, after the first fusion step between the anionic DOPS liposome and the naked cationic silica core, the following steps involved lipid exchange; otherwise, e.g., for fusion or adsorption, the potential of the protocells and liposomes should be identical to those of pure liposomes.

When DOPS liposomes are fused with cationic silica nanoparticles, defects are likely to form, and these are difficult to heal because of electrostatic considerations. Subsequent addition of cationic DOTAP liposomes resulted in electrostatically-driven association and lipid exchange up until the point where the diminishing electrostatic interaction and van der Waals attraction are exceeded by the disjoining pressure, after which the associated exchanged liposome was released.

Confocal fluorescence microscopy (CFM) and transmission electron microscopy (TEM) were used to measure the liposome fusion of a first liposome on the porous particle core and lipid exchange by a second liposome. About 15 μm anionic mesoporous silica particles were fused first with Texas Red-labeled DOTAP and then mixed with NBD-labeled DOPS. Co-localization of the red and green fluorescence established the presence of both DOTAP and DOPS. Corresponding TEM of fixed and stained protocells showed that the majority of particles, after both the initial fusion step and subsequent exchange steps, had an about 5.5-nm-thick rim, indicative of a single supported bilayer, while a very small fraction of particles, less than about 1%, had a layer about 11-nm-thick, indicative of dual bilayers. Therefore, while a majority of the particles underwent lipid exchange, fusion can not be completely ruled out. Double bilayer fusion was never observed in a single step.

Example 7

Enhanced Fluidity of SLB

To illustrate the aspects of long-range fluidity of porous particle-supported lipid bilayers (SLBs), temperature-dependent fluorescence recovery after photobleaching (FRAP) results were collected for an exemplary protocell having a DPPC lipid bilayer supported on a nanoporous silica particle and for a SLB supported on a solid glass i.e. non-porous silica particle. A photobleached region (not shown) was observed to recover at 35° C. (±1° C.) for the protocell compared to 41° C. (±1° C.) measured for the SLB on the solid glass silica particle, indicating a dramatic reduction (by 6° C.) of the membrane fluidization temperature $T_m$, corresponding to the gel-to-fluid main phase transition temperature. This suppression of the melting point was a consequence of physical constraints at the interface between the lipid bilayer and the porous particle core support in the protocells or protocell compounds.

Examples 8

SLB Composition Vs. Non-Specific Binding

Non-specific affinity of protocell compounds modified with 0.500 wt % of the SP94 targeting peptide (2048 peptides/particle) for Hep3B and hepatocyte cells was a function of the charge and fluidity of lipids employed in the SLB of the protocell compounds and the degree to which the SLB is modified with shielding materials, e.g. PEG.

The affinity of SP94-targeted DOPC, DPPC, DOTAP, and DOPG protocells for Hep3B and hepatocytes, with shielding materials used, was tested by total binding, non-specific binding, and specific binding.

Total binding was defined as the mean fluorescent intensity (MFI) of cells exposed to a saturating concentration of SP94-targeted protocells (labeled with 1 wt % Texas Red DHPE), while non-specific binding was defined as the MFI of cells exposed to a saturating concentration of unmodified protocells (labeled with 1 wt % Texas Red DHPE). Specific binding was the difference between total binding and non-specific binding.

Protocells coated with lipids that have a positive charge (DOTAP) or negative charge (DOPG) have increased undesired non-specific binding to both HCC and hepatocytes. Employing zwitterionic lipids in the SLB minimized non-specific binding and maximized specific binding, and DPPC protocells had a slightly lower non-specific affinity for Hep3B and hepatocytes than DOPC protocells.

Shielding materials included in the lipid bilayer, and the affinity of DOPC, DOPC with 30 wt % cholesterol, DOPC with 5 wt % PEG-2000, DPPC, DPPC with 30 wt % cholesterol, and DPPC with 5 wt % PEG-2000 protocells for Hep3B and hepatocytes was measured. Incorporating cholesterol or PEG-2000 PE into the SLB further reduced the non-specific binding of DOPC and DPPC protocells to Hep3B and hepatocytes.

Examples 9

Fluid SLB Vs. Targeting Specificity

Protocells were prepared by liposome fusion onto spherical ~120-nm diameter nanoporous silica cores loaded with dyes, drugs, or other components.

Based on optimization studies of stability and non-specific binding conducted in a simulated body fluid, the composition of the supported lipid bilayer used throughout the experiments was (by weight) about 30% cholesterol, about 5% PEG 2000, about 5% DOPE, and the remainder DOPC ($T_m$=−20° C.) or DPPC ($T_m$=41° C.). Using a heterobifunctional crosslinker with a PEG (n=8) spacer, SP94 peptides ($H_2N$—SFSIILTPILPL-COOH (SEQUENCE ID NO. 3), identified via filamentous phage display to have an affinity for unknown receptor(s) expressed by human HCC) were covalently attached to DOPE head groups at concentrations ranging from about 0.002 to about 5.0 wt %, corresponding on average from 1 to about 2048 peptides per particle. Equivalent 120-nm liposomes were synthesized for comparative purposes.

Dissociation constants, $K_d$, where $K_d$ is inversely related to binding affinity, between protocells or liposomes and HCC or normal hepatocytes or other negative control cells were determined using flow cytometry at 4° C., where no accompanying internalization was observed.

Plotting $K_d$ as a function of peptide coverage, fluid DOPC protocells had a high specific affinity ($K_d$<1 nM) for HCC and, over the range of 6 to 2048 peptides per particle, their $K_d$ values were consistently low (about 0.94 nM to about 0.08 nM) and relatively independent of peptide density. In comparison, for solid DPPC protocells and liposomes, over an order of magnitude higher $K_d$ was measured, and a strong peptide density dependence of $K_d$ was measured at low densities, i.e. approaching that of the monovalent peptide (1 peptide per particle).

For DOPC protocells, the high binding affinities and low peptide density dependence were attributed to recruitment of multiple SP94 peptides to the HCC cancer cell surface, enabled by the fluid SLB. For solid DPPC protocells and liposomes, this multivalent effect and correspondingly low $K_d$ were realized only at high peptide density due to kinetic constraints imparted by the non-fluid lipid bilayer.

In experiments, NBD-labeled DOPC or DPPC liposomes were fused to a planar nanoporous substrate (with a 3D pore structure prepared by evaporation-induced self-assembly and comparable to that of the protocell core) and modified with a low density (~0.015 wt %, equivalent to 6 peptides per particle in the $K_d$ measurements) of Alexa Fluor 647®-labeled SP94 peptides. Upon introduction of a HCC cell line (Hep3B) to the supported planar bilayers at 4° C., rapid (1-2 minutes) recruitment of SP94 peptides to the cancer cell surface was observed for the fluid DOPC supported bilayer, with no measurable recruitment for the solid DPPC bilayer.

Comparing the peptide density dependent $K_d$ values of DOPC liposomes and protocells for HCC and normal hepatocytes, DOPC protocells modified with ~6 copies of the SP94 peptide had a differential $K_d$ (HCC over hepatocytes) of >2×10$^4$, exceeding that of targeted DOPC liposomes by >10$^2$. This emphasizes that protocells possessing a fluid SLB selectively target HCC (but not normal cells) at low SP94 densities. The <10$^4$ differential binding affinity for HCC over hepatocytes was also measured for other negative control cells, including human endothelial cells (HUVECs) and immune cells (PBMCs and B- and T-lymphocytes).

The $K_d$ value of targeted DOPC protocells for Hep3B was 2000-fold lower than that of free SP94 for Hep3B, and nearly 50.000-fold lower than that of unmodified protocells for Hep3B.

Examples 10

Fluid SLB Vs. Internalization

Upon warming to 25 or 3TC, the differential binding affinity of HCC over hepatocytes was translated into differential internalization efficiency. Fluid DOPC protocells modified with SP94 targeting ligands were efficiently endocytosed by Hep3B but not by normal (i.e. untransformed) hepatocytes. A size dependence of internalization efficiency was also observed, with 30-60 nm protocells yielding the highest average number of internalized protocells per Hep3B cell at 3TC.

Examples 11

Targeted Delivery of Multicomponent Cargos

Various fluorescently-labeled surrogates (similar in size and charge to therapeutic or diagnostic agents of interest) were encapsulated within the protocell core by simply soaking the nanoporous particles in a solution of the desired cargo prior to fusion of DOPC liposomes and conjugation of SP94 peptides to the SLB. For example, calcein, a low molecular weight drug mimic; a double-stranded DNA oligonucleotide, an siRNA mimic; red fluorescent protein, a protein toxin mimic; and far red-fluorescent quantum dots can be simultaneously encapsulated within a fluorescently-labeled silica particle to which fluorescently-labeled DOPC liposomes are fused to trap cargo in the core. Confocal fluorescence microscopy of a protocell 10 μm in diameter (used for demonstration purposes to enable optical imaging) was employed to show uniform distribution of the multiple cargos within the silica core and a uniform coherent SLB.

Example 12

Drug Delivery and Cytotoxicity

High payloads of various cytotoxic agents, including drugs and drug cocktails, siRNA cocktails and protein toxins were delivered to Hep3B without affecting the viability of control cells. The cargo capacity, release characteristics, and cytotoxicity of the chemotherapeutic drug doxorubicin (DOX) were measured for targeted DOPC protocells and compared to corresponding loaded DOPC liposomes synthesized with identical lipid bilayer compositions.

Example 12.1

Cargo Capacity

Due to the large volume fraction porosity (~50%) and high surface area (>1000 m$^2$/g) of nanoporous silica cores, protocells have a 1000-fold higher cargo capacity for DOX than similarly sized liposomes loaded via an ammonium phosphate gradient-based approach. Due to their high capacity for drugs, about 2×10$^7$ doxorubicin-loaded DOPC protocell compounds prepared with a low peptide density (~6 peptides/protocell or 0.015%) and stabilized with PEG were needed to kill 90% of Hep3B (1×10$^6$ cells/mL) with induced MDR (LC$_{90}$). 10$^5$ more doxorubicin-loaded DOPC liposomes are necessary to achieve the LC$_{90}$ value.

Example 12.2

Release Characteristics

Figure 4A:
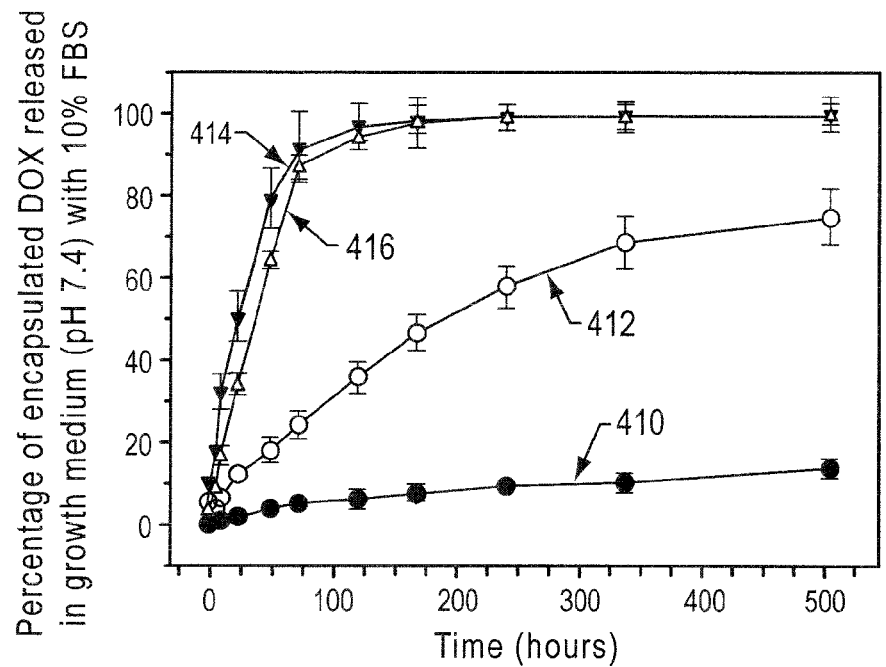
FIGS. 4A-4B depict time-dependent release profiles of exemplary targeted protocell compounds in accordance with various embodiments of the present teachings.

FIG. 4A depicts a time-dependent release profile of DOX from DOPC protocells (see 410), DSPC liposomes (see 412), DOPC liposomes (see 414), and nanoporous cores (see 416), when exposed to a simulated body fluid (pH 7.4) at 3TC.

As shown, protocells exhibited long-term stability over several hundred hours when maintained in a neutral pH simulated body fluid at 37° C. Conversely, under neutral conditions, DOPC liposomes released nearly all of their encapsulated DOX within 72 hours (see 414), their release profile being comparable to that of the nanoporous protocell core without a SLB (see 416). Thus, the fluid lipids (e.g., DOPC) that enable selective targeting at low peptide densities cannot be used in liposomal drug formulations, since pre-mature release of encapsulated cargo components resulted in non-specific toxicity to normal cells; stable formulations of liposomal drugs required the use of fully saturated, high T$_m$ lipids and high concentrations of cholesterol, which act cooperatively to increase the lipid packing density and limit diffusion of the drug across the lipid bilayer. Even the stability of 'gold standard' liposomal doxorubicin (e.g. DSPC with 30 mol % cholesterol, loaded using an ammonium sulfate gradient approach) remained limited, however, as up to 30% of the drug was released within 72 hours when exposed to a simulated body fluid at 37° C.

Figure 4B:
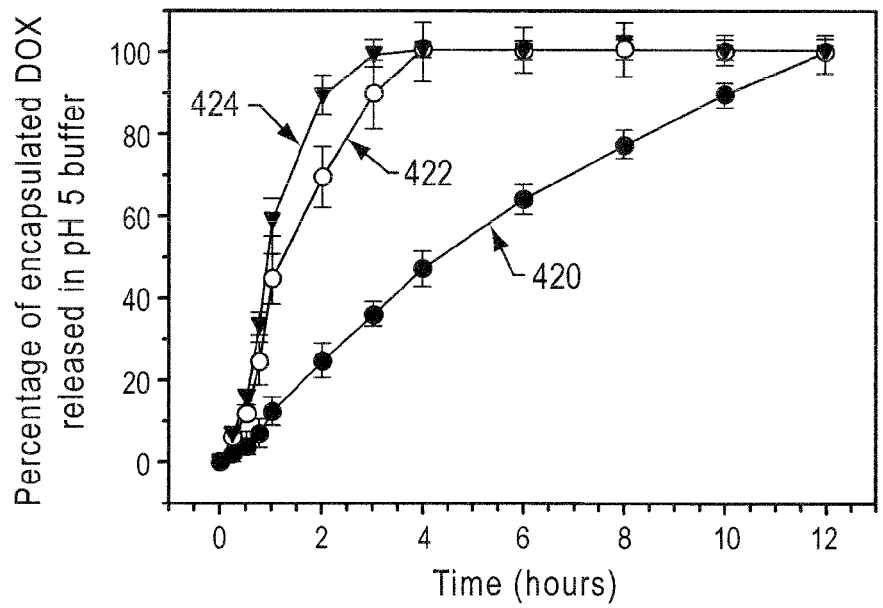

FIG. 4B depicts a time-dependent release profile of DOX from DOPC protocells (see 420), DSPC liposomes (see 422), and DOPC liposomes (see 424), when exposed to a pH 5 citric acid buffer at 37° C. Acidic conditions mimicked those of the endosome and destabilized the SLB, thereby promoting release of DOX from the nanoporous core.

As shown in FIG. 4B, reducing the pH to 5 simulated the endosomal environment and destabilized the SLB, resulting in rapid release of encapsulated DOX. Although liposomes (see 424) exhibited a higher release rate of DOX at pH 5, the much greater capacity of protocells (5000×) resulted in a ~2500× greater DOX release after ~12 hours.

Example 12.3

Cytotoxicity of the Chemotherapeutic Drug Doxorubicin (DOX)

Concentration-dependent cytotoxicity of SP94-targeted protocells and liposomes that encapsulate chemotherapeutic drugs (DOX) were measured. For example, the percentage of Hep3B or hepatocytes that remained viable after exposure to 10 μM DOX-loaded DOPC protocells or liposomes for 24 hours was measured. Sytox® Green nucleic acid stain and Alexa Fluor 647®-labeled annexin V were used to distinguish viable (double-negative) from non-viable (single- or double-positive) cells. Targeted DOPC protocells were cytotoxic to MDR Hep3B but not to hepatocytes. Specifically, protocells were observed to maintain greater than 90% hepatocyte viability, while killing over 95% of MDR Hep3B. By comparison, liposomes were less efficient at killing Hep3B and showed significant cytotoxicity to normal cells.

Protocells were easily loaded with multicomponent cargo components by simple soaking of the nanoporous core in a solution of the desired cargo(s) prior to liposome fusion. For example, when loaded with a cocktail of DOX, 5-fluorouracil, and cisplatin (a chemotherapeutic drug cocktail known to be particularly effective against HCC), as few as one SP94-modified protocell was sufficient to kill a Hep3B cell with induced MDR while maintaining about 90% hepatocyte viability. In comparison, targeted liposomes could not be loaded with the multicomponent cargo using osmotic gradient or other loading strategies.

Example 13

Lack of Antibody Responses to Peptides on Protocells

The induction of antibodies against a targeting peptide may interfere with the ability to deliver cargo components to target cells. To assess this possibility, mice were injected with SP94-modified protocells and then IgG antibody responses were quantitated. As a control, a group of mice was also immunized with the SP94 peptide displayed at roughly the same density on another multivalent display platform, bacteriophage MS2 virus-like particles (VLPs). MS2 VLPs conjugated with SP94 induced high titer IgG responses against the peptide, while protocells displaying SP94 did not induce IgG antibodies against SP94.

While the present teachings have been illustrated with respect to one or more implementations, alterations and/or modifications can be made to the illustrated examples without departing from the spirit and scope of the appended claims. In addition, while a particular feature of the present teachings may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." As used herein, the term "one or more of" with respect to a listing of items such as, for example, A and B, means A alone, B alone, or A and B. The term "at least one of" is used to mean one or more of the listed items can be selected.

Notwithstanding that the numerical ranges and parameters setting forth the broad scope of the present teachings are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume values as defined earlier plus negative values, e.g. −1, −1.2, −1.89, −2, −2.5, −3, −10, −20, −30, etc.

Other embodiments of the present teachings will be apparent to those skilled in the art from consideration of the specification and practice of the present teachings disclosed herein. It is intended that the specification and examples be considered as exemplary only, with a true scope and spirit of the present teachings being indicated by the following claims.

What is claimed is:

1. A protocell comprising:
    a porous silica nanoparticle core comprising a plurality of pores, said nanoparticle core being formed from an aqueous precursor mixture comprising tetraethylorthosilicate (TEOS) and an amine-modified silane precursor, said porous silica nanoparticle core having an average particle size ranging from about 30 nm to about 3000 nm; and
    a supported lipid bilayer encasing the porous particle core and supported by the porous particle core,
    wherein said lipid bilayer consists essentially of a zwitterionic phosphoholipid selected from the group consisting of 1,2-dioleoyl-sn-glycero-3-phosphocholine (DOPC), dipalmitoylphosphatidylcholine (DPPC) and a mixture thereof, and wherein said protocell, after administration to a subject, decreases non-specific binding of said protocells in said subject when compared to protocells which are encased with a lipid bilayer comprising positively or negatively charged phospholipids.

2. The protocell according to claim 1 wherein said amine-modified silane precursor is selected from the group consisting of 3-2[2-(2-aminoethylamino)ethylamino]propyltrimethoxysilane (AEPTMS), 3-aminopropyltrimethoxysilane (APTMS)nanostructure and a mixture thereof and said amine-modified silane precursor comprises about 5% to about 30% by weight of said precursor mixture.

3. The protocell according to claim 1 wherein the lipid bilayer is fused to the porous particle core and has a melting transition temperature $T_m$ which is less than that of a corresponding lipid bilayer which is unsupported or supported without fusion.

4. The protocell according to claim 1 wherein said zwitterionic phospholipid is DOPC or a mixture of DOPC and DPPC.

5. The protocell according to claim 1 wherein said zwitterionic phospholipid is DOPC.

6. The protocell according to claim 1 wherein the plurality of pores has an average pore size ranging from about 2 nm to about 30 nm.

7. The protocell according to claim 4 wherein the plurality of pores has an isotropic wormlike nanoporosity.

8. The protocell according to claim 1, wherein said lipid bilayer has a thickness ranging from about 1 nm to about 5 nm.

9. The protocell according to claim 1 further comprising one or more cargo components is disposed within the porous particle core and a targeting ligand attached to the lipid bilayer for increasing selective binding of said protocell to a target cell; and an optional shielding material attached to the lipid bilayer for reducing non-specific binding to the target cell and non-target cells.

10. The protocell according to claim 1 wherein a fusogenic peptide is attached to the lipid bilayer, the fusogenic peptide comprising a histidine-rich fusogenic peptide H5WYG having a sequence of SEQ ID NO:1.

11. The protocell according to claim 9 wherein a fusogenic peptide is attached to the lipid bilayer, the fusogenic peptide comprising a histidine-rich fusogenic peptide H5WYG having a sequence of SEQ ID NO:1.

12. The protocell according to claim 9 wherein said one or more cargo components are selected from the group consisting of protein toxins, plasmid DNAs, siRNAs, nanoparticles, diphtheria toxins, doxorubicins, 5-fluorouracils, cisplatins and mixtures thereof.

13. The protocell according to claim 9 wherein said shielding material is selected from the group consisting of polyethylene glycol, cholesterol and mixtures thereof.

14. The protocell according to claim 9 wherein said one or more cargo components is DNA or RNA.

15. The protocell according to claim 14 wherein said cargo component is DNA.

16. The protocell according to claim 14 wherein said cargo component is RNA.

17. The protocell according to claim 1 wherein said amine-modified silane precursor is selected from the group consisting of 3[2-(2-aminoethylamino)ethylamino]propyltrimethoxysilane (AEPTMS), 3-aminopropyltriethoxysilane (APTES) and a mixture thereof and said amine-modified silane precursor comprises about 5% to about 30% by weight of said precursor mixture.

* * * * *